United States Patent [19]
Goldstein

[11] Patent Number: 4,643,814
[45] Date of Patent: * Feb. 17, 1987

[54] STRUCTURE SELECTIVE FIBROUS SORBENTS AND METHOD AND APPARATUS FOR USING THE SAME

[75] Inventor: Arthur L. Goldstein, Weston, Mass.

[73] Assignee: Ionics, Incorporated, Watertown, Mass.

[*] Notice: The portion of the term of this patent subsequent to Jun. 10, 2003 has been disclaimed.

[21] Appl. No.: 722,968

[22] Filed: Apr. 12, 1985

Related U.S. Application Data

[63] Continuation-in-part of Ser. No. 703,581, Feb. 20, 1985, Pat. No. 4,594,135.

[51] Int. Cl.$^4$ .............................................. B01D 13/02
[52] U.S. Cl. ............................ 204/180.1; 204/182.3; 204/182.4; 204/299 R; 204/301; 204/182.6
[58] Field of Search .............. 204/180.1, 182.3, 182.6, 204/149, 151, 242, 263, 299 R, 301

[56] References Cited

U.S. PATENT DOCUMENTS

| 3,730,885 | 5/1973 | Makrides et al. | 204/149 |
| 3,966,580 | 6/1976 | Janata et al. | 204/296 |
| 4,151,049 | 4/1979 | Janata | 204/296 |
| 4,400,250 | 8/1983 | Fairhurst | 204/151 |

Primary Examiner—Terryence Chapman
Attorney, Agent, or Firm—Norman E. Saliba

[57] ABSTRACT

Processes and apparatuses are described for recovering components dispersed in an aqueous solution, the process comprising contacting said solution as a first solution with a body of filaments, fibers, hair-like objects or other thread-like objects which have a high affinity for at least one of said components whereby a substantial fraction of said component is sorbed by said body. The body is subsequently contacted with a second aqueous solution as a receiving solution; such second solution comprising agents for facilitating the desorption of at least one of said selected components from the body into said second solution. The desorbed components are then separated from said body.

23 Claims, 4 Drawing Figures

STRUCTURE SELECTIVE FIBROUS SORBENTS AND METHOD AND APPARATUS FOR USING THE SAME

This application is a Continuation-In-Part of U.S. patent application Ser. No. 703,581 now U.S. Pat. No. 4,594,135 filed Feb. 20, 1985 entitled "Process and Apparatus for Electrically Desorbing Components Selectively Sorbed on Granules" and assigned to the same assignee as this application.

BACKGROUND OF THE INVENTION

1. Field of the Invention

Affinity chromatography has become a valuable tool for separating biological materials, for example, biologically active molecules such as small ligands, proteins, nucleic acids, enzymes, etc. In affinity chromatography, a substrate is immobilized on a granular support. By utilizing a column of said granular, immobilized substrate, materials having affinity, structure selectivity, or binding specificity for the compounds bonded to the stationary phase can be separated from other materials in an aqueous mixture thereof.

Typically, complex polysaccharide granules such as agarose beads, etc. are employed in affinity chromatography. The material of the granules may inherently have the desired sorption specificity or a suitable ligand may be bonded, often through so-called spacer-arms, to the granules by a variety of methods. Components in an ambient solution which have a high binding affinity for the materials of the granules or for the ligand will be preferentially bound to the granules. The bound components may be subsequently removed from the granules by contacting the latter with reagents which reduce the binding of the component for the material of the granules or for the ligand. Typically such desorption is accomplished by a substantial change in pH or ionic strength or both. Alternatively the sorbed component may be desorbed by another ligate which competes for the binding sites. Often chaotropic agents are used which, apparently, by altering the secondary structure of the sorbed component effect desorption.

Examples of highly specific ligands are:

Lectin absorbents for binding glycoproteins, glycolipids, polysaccharides, and related substances;

Protein A from Staphylococcus aureus for binding many immunoglobulins;

Cibacron ® Blue F3G-A for binding albumin, interferons, growth factors, kinases and dehydrogenases;

Monoclonal antibodies for binding biospecific antigens;

Biospecific antigens for binding monoclonal antibodies; and

Hydrophobic groups (e.g. aliphatic or aromatic moieties) for binding proteins having hydrophobic regions.

Desorption of tightly bound, high molecular weight ligates is generally a rather slow process, particularly in porous granules or beads, and in the presence of substantial changes in pH, ionic strength or high concentrations of chaotropic reagents may result in alterations in biological activity of the ligate or loss of biospecificity of the ligands.

It is an object of the present invention to provide processes and apparatuses which enable easy handling of the biospecific substrate and the comparatively rapid and economic recovery of bioactive ligates under comparatively gentle desorption conditions, thereby preserving a substantial fraction of the bio-activity.

These and other objects will become apparent from the following description of the invention.

2. Description of the Prior Art

The prior art is well described in:

(a) "Affinity Chromatography" by W. H. Scouten, John Wiley & Sons, Inc., New York, 1981;

(b) "Affinity Chromatography" by J. Turkova, Elsevier, Amsterdam, Netherlands, 1978;

(c) "Affinity Chromatography, Principles and Methods", Pharmacia Fine Chemicals AB, Uppsala, Sweden; and (d) "Kirk-Othmer Encyclopedia of Chemical Technology, 3rd Edition, Vol 6, page 35 et. seq.

Typical support materials for affinity chromatography are granular and bead-like gels of agarose, cross-linked agarose, polyacrylamide and dextranepichlorohydrin. They are high cost, soft and compressible which make them unattractive for large scale processes. Rigid supports can be made from porous glass or ceramic beads which are coated to reduce non-specific protein binding. These are technically suited for large scale processes but are even more expensive than gel beads and granules.

To obtain high binding capacities with bead or granular supports it is necessary to use the interior as well as the exterior area of the support, that is, the support must have high porosity for the typically high molecular weight materials sorbed. However, access to such interior surfaces is very slow for high molecular weight sorbates leading to long sorption and desorption times. Since desorption often requires pronounced changes in pH or ionic strength and/or the presence of chaotropic agents, long desorption times can lead to irreversible changes in the secondary structure of the ligates and/or ligands. However, access to such interior surfaces is very slow for high molecular weight sorbates leading to long sorption and desorption times. Since desorption often requires pronounced changes in pH or ionic strength and/or the presence of chaotropic agents, long desorption times can lead to irreversible changes in the secondary structure of the ligates and/or ligands. Polyacrylamide and dextranepichlorohydrin gels with suitable mechanical properties typically have low molecular porosity.

U.S. patent application Ser. No. 675,057 now U.S. Pat. No. 4,584,075 filed Nov. 26, 1984, entitled "Process and Apparatus for Electrically Desorbing Components Selectively Sorbed on Electrolytic Conducting Barriers" and assigned to the same assignee as this patent application, discloses processes and apparatuses for recovering components dispersed in an aqueous solution comprising contacting said solution as a first solution with an electrically conductive barrier which has a high affinity for one of said components. The barrier is subsequently contacted with a second aqueous solution and a direct electric current is passed through said barrier in a direction substantially perpendicular to the barrier and to the flow of solution thereby resulting in the substantial desorption of the sorbed component. Said application does not disclose recovering components sorbed on a body of fibrous objects which have a high affinity for at least one of said components.

U.S. patent application Ser. No. 703,581 now U.S. Pat. No. 4,594,135, filed Feb. 20, 1985, entitled "Process and Apparatus for Electrically Desorbing Components Selectively Sorbed on Granules" (of which the present invention is a Continuation-In-Part and assigned to the same assignee as this patent application) discloses process and apparatus for recovering components sorbed on a body of wet granules which are highly selective for the sorption of said components. The process comprises passing a direct electric current through said body of granules and an ion-permeable, substantially hydraulically impermeable barrier juxtaposed with said body of granules in a direction substantially parallel to the smallest dimension of said barrier, thereby facilitating the desorption of at least one of said selected components from said granules.

All the prior art substrates summarized above suffer from high cost and/or, if they contain high available surface areas, poor mechanical properties. If such substrates have high internal surface areas then undesirably long sorption and desorption times will be experienced for high molecular weight ligates, often leading to substantial denaturation of the ligate and/or ligand.

It is therefore a further objective of this invention to provide substrates having low cost per unit volume and good mechanical properties. It is also an objective to provide apparatuses and methods for using such substrates in affinity separations.

These and other objectives will become clear from the following brief description of the drawings and description of preferred embodiments.

DESCRIPTION OF PREFERRED EMBODIMENTS

In its broadest aspect, the present invention consists of a biospecific sorbing fibrous substrate in the form of continuous filaments, staple fibers, gauze, screen, woven-fabric, knitted-fabric, non-woven fabric, felts, fiber-mats, needled felts, threads, string, yarn, tow, filter-masse, batting, roving, sliver, cake-of-fibers and the like.

Figures 1, 2:
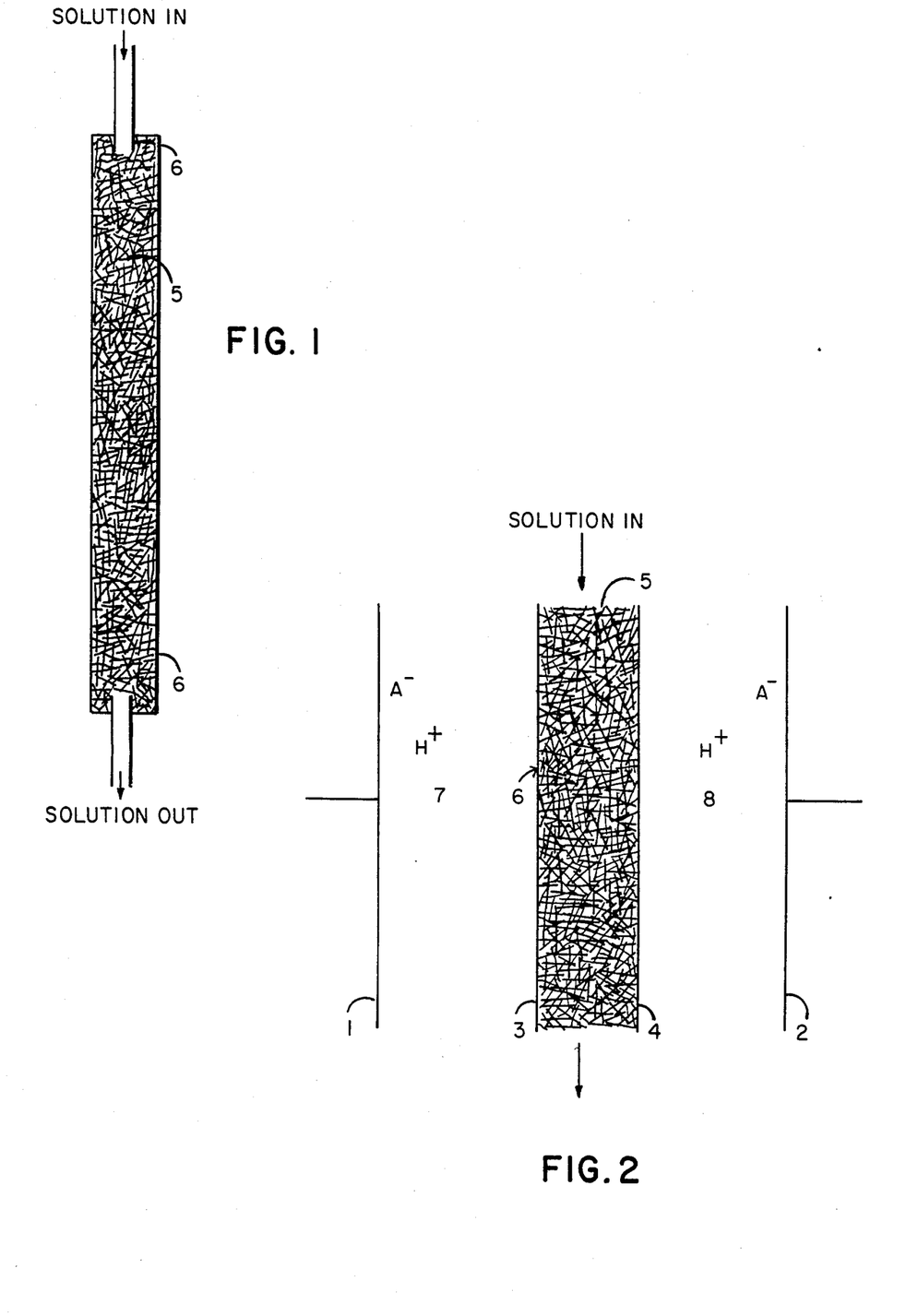
FIG. 1 is a schematic representation of one embodiment of an apparatus having a biospecific sorbing fibrous substrate in accordance with this invention.
FIG. 2 is a schematic representation of another embodiment of an apparatus having a biospecific sorbing fibrous substrate juxtaposed against at least one electrolytically conducting, ion-permeable, substantially hydraulically impermeable barrier (which may also be biospecifically sorbing) in accordance with the present invention.

Referring to FIG. 1, there is indicated a container 6 having entrance and exit conduits and packed with a body of fibrous, biospecifically sorbing substrate 5. The fibrous substrate may have inherent biospecific sorbent properties as in the case of zein, collagen, and materials containing transitional metal chelates; or the substrate may be coated with such inherently biospecific sorbing substances; or biospecific ligands may subsequently be added to the surface of the substrate. Such ligands may be more or less permanently sorbed on the substrate, as for example, certain antibodies can be sorbed on the surfaces of zein or collagen fibers (or fibers coated with zein or collagen) by incubating the latter for prolonged periods in a dispersion of the former. It appears that secondary bonds (which were previously formed within antibody moieties and between the zein or collagen molecules) form between the antibody and the zein or collagen. On the other hand the fibrous substrate may be activated in various ways know in the art, for example with cyanogen bromide, trichloro-s-triazine, isocyanate, glutaraldehyde and the like as is appropriate to the fibrous substrate and the desired ligand. As a third alternative, the fibrous substrate may inherently comprise, contain or be coated with active moieties such as terpolymers of methacrylamide, allyl-glycidyl-ether and N-methylene-bis methacrylamide. Suitable activating agents or active moieties are well known in the art. The ligands may be bound directly to the surface of the fibrous substrate or through leashes, tethers, spacer-arms or other stand-offs depending primarily on the size of ligand or target ligate. Suitable stand-offs are well known in the art.

Preferred ligands show a high structural selectivity for the desired ligate and also possess second functional sites at which immobilization to the fibrous substrate may be affected without substantially affecting ligate binding. Depending on the target ligate, a wide variety of ligands may be used. The following table illustrates the various classes, but is not intended to limit the scope of this invention.

| Target Ligate | Suitable Ligand |
| --- | --- |
| 1. Enzymes, apoenzymes | Inhibitor, cofactor, prosthetic group, polymeric substrate |
| 2. Polymeric inhibitors | Enzymes |
| 3. Nucleic acid, single strand | Nucleic acid complementary strand |
| 4. Antibody | Hapten, antigen |
| 5. Proteins, polysaccharides | Antibody |
| 6. Lectins, receptors | Monosaccharide, polysaccharide |
| 7. Glycoproteins, Receptors | Lectin |
| 8. Binding proteins | Small target compounds |
| 9. Small target compounds | Binding protein |
| 10. Trypsin, thrombin, urokinase | Aminobenzamide |
| 11. Nicotine adenine dinucleotide dependent dehydrogenases | 5'-adenosine monophosphate |
| 12. Immunoglobulin G | *S. aureus* Protein A |
| 13. Albumin, coagulation factors, interferon | Cibacron ® Blue F3G-A |
| 14. Serum proteins, interferon | Chelated transition metals |
| 15. Lactalbumin, catalase ferritin, cytochrome C | Octyl or phenyl moieties |

Suitable fibrous substrates include, without limitation, cotton, linen, jute, hemp, sisal, ramie, henequen, abaca, coir, kapok, wood pulp, cellulose crumb (all of which may be bleached), wool, alpaca, mohair, vicuna, silk and other animal hairs, rayon, acetate, azlon (regenerated protein), partially hydrolyzed acrylic or modacrylic, aramid, nylon, glass and polybenzimidazole in the form (as appropriate) of fibers, filaments (continuous or finite), string, yarn, tow, filtermasse, butting, roving, sliver, cake-of-fiber woven-fabric, fiber-mat, felt, needled-felt, screen and gauze which have natural biospecific sorbing properties or can be activated or modified in appropriate ways to have biospecific sorbing properties. Fibers which are not inherently biospecific sorbing or which have not been activated or modified to introduce biospecific sorbing properties can be included with fibers which have biospecific sorbing properties in order to introduce desirable mechanical properties, for example in the case of bonded mats.

The above fibrous substrates (and others) may be treated or coated to impart biospecific sorbing properties or to facilitate the introduction of stand-offs, activating agents or biospecific sorbing moieties.

Such biospecific sorbing fibrous substrates are particularly useful in "teabags" and continuous belt or ribbon affinity separations.

The advantage of fibrous material as substrate for affinity separation may be seen by noting that 1 gram of 3 denier fiber has a surface area of about 1800 cm. Typically such fibers have a price of less than two dollars per pound, that is about 400,000 cm of surface can be purchased for less than one dollar.

A preferred method of using the above described apparatus is as follows:

The aqueous solution or suspension containing the target molecules is passed or circulated through the body of biospecific fibrous substrate either within the apparatus of this invention or external thereto. In the latter case the sorbed substrate is subsequently loaded into the apparatus.

When the biospecific capacity of the fibrous substrate has been substantially saturated and/or the ligate containing solution or suspension has been substantially depleted of target ligate(s), the solution or suspension is withdrawn from further contact with the substrate and the latter rinsed with pure water or other appropriate aqueous solutions to remove traces of the ligate containing solution or suspension and/or to remove nonspecifically sorbed components from the substrate. If the sorption step was carried out external to the apparatus, the sorbed substrate is then loaded into the apparatus. The apparatus is then ready for desorption of one or more of the sorbed ligates with the facilitation of a desorbing agent.

Several desorption modes are contemplated. One of these may be described with reference to FIG. 1 in which 6 represents a container with inlet and outlet means and 5 represents a body of biospecific fibrous substrate. A solution of appropriate desorption facilitating agent (e.g. a dilute solution of a strong acid, a weak acid or of an acidic buffer; a solution of high ionic strength; a solution of a competing ligate or ligand; a solution of a chaotropic agent (such as sodium thiocyanate or guanidine hydrochloride) is passed through or circulated through the container. The target ligate is susequently recovered from the desorption facilitating solution.

A second desorption mode may be described with reference to FIG. 2 in which 6 represents a compartment comprising a body of biospecific fibrous substrate 5 juxtaposed to a barrier 3 and a barrier 4; 7 represents a compartment defined between the barrier 3 and the electrode 1 (or in the case where several barriers are arranged between a single pair of electrodes, the compartment defined between the barrier 3 and another barrier generally similar in properties to barrier 3). In the embodiment of this invention represented in FIG. 2, compartment 7 is filled with an appropriate acid solution which may be, for example, a dilute solution of a strong acid, a weak acid or of an acidic buffer. Compartment 6 is filled with or wet with an appropriate liquid, the choice depending on both the ligand(s) and the ligate(s), generally a buffer solution or pure water. Electrode 1 is made anodic and electrode 2 cathodic causing the transport of hydrogen ions across the barrier 3 (which is preferably cation-selective or non-selective) into the fibrous substrate 5 in compartment 6. In a preferred method of operation, the electric current is continued for a period sufficient to reduce the pH in the body of fibrous substrate to a value at which the ligate-ligand complex is dissociated and the ligate begins to diffuse away from the fibrous substrate into the liquid remaining in compartment 6. According to such preferred method, the liquid in compartment 6 is not flowing during the period in which the electric current flows. It will be understood that the interstices in the body of fibrous substrate need not be filled with liquid if the moist substrate (for example containing sorbed liquid) is electrolytically conducting. Again in accordance with said method, after the flow of electric current ceases (or is reduced to a maintenance value), the diffusion of the dissociated ligate(s) into the liquid may be allowed to continue for some minutes before the contents of compartment 6 are removed. The duration of such diffusion period depends on the diffusion constant(s) of the ligate(s) (and therefore generally on the molecular weight), but is generally sufficiently long to permit a substantial fraction of the ligate to diffuse away from the substrate. Compartment 6 is then drained, or rinsed, preferably by imposing a flow of liquid through the compartment. In this way the first compartment volume of liquid issuing from compartment 6 will contain a substantial fraction of the dissociated ligate at a comparatively high concentration.

It will be seen that by this method, particularly if the thickness of the body of fibrous substrate is substantially less than its width or length, the dissociating reagent is applied rapidly to the biospecific substrate and the dissociated ligate(s) (and ligand) is (are) exposed to the dissociating entity for only a short period of time compared with the conventional affinity chromatography methods using porous granules. It is found therefore that the dissociating conditions are particularly gentle and comparatively little denaturation of the ligate occurs, resulting in higher recoveries (yields) of bioactivity.

Referring again to FIG. 2, it will be understood that if the sorbing groups and the ligands sorbed thereon are not sensitive to the electrolysis products of one of the electrodes then the adjacent barrier may be eliminated in which case the fibrous substrate may be in contact with the electrode.

The barriers may comprise inherently electrolytically conducting, substantially hydraulically impermeable material such as an ion exchange resin in the form of sheets or films; hydrous material such as a hydrated gel; or a microporous material containing water or an aqueous solution in the pores. Examples of suitable hydrous material are agarose gels, zein, collagen, and polyacrylamide gels in the form of sheets. Other suitable hydrous gels will be obvious to those skilled in the art. The sheets are preferably reinforced with woven or nonwoven fabrics to improve the mechanical strength and handling properties.

Examples of suitable microporous materials are films of Cuprophan, regenerated cellulose, cellulose acetate and nylon; or inorganic diaphragms such as ceramic diaphragms, all generally having average pore sizes less than about 10 micrometers which inhibit convective mixing of liquids through the barrier.

Optionally the barrier may also have biospecific sorbent properties in which case its composition will ideally be similar to that of the biospecific sorbing granules with which it is in contact. It will be understood that the barrier and granules may have different compositions and even different biospecific sorbent properties as long as the differences are not incompatible with respect to the desired separation.

The operation of the apparatus of FIG. 2 has been described by reference to effecting an alteration of pH in the biospecific fibrous substrate. Alternatively, compartment 7 may contain a chaotropic agent such as guanidine hydrochloride in which case guanidinium cations will be transferred across the barrier (which should then not be anion-selective) to the biospecific substrate resulting in dissociation of the ligate(s). Subsequent steps in the operation will be substantially as described above. Dissociation may also be effected by causing a substantial change in the ionic strength in the biospecific substrate by passage of electric current. This is particularly effective and efficient when the barrier 3 is ion selective, for example when it comprises an ion exchange resin. If the ligate will be dissociated by an increase in ionic strength and if the barrier 3 is cation selective, then electrode 1 should be anodic and electrode 2 cathodic. It will be obvious to those skilled in the art that if barrier 3 is anion selective then electrode 1 should be cathodic and electrode 2 anodic. On the other hand if the ligate will be dissociated by a decrease in ionic strength (as, for example, when the ligands are hydrophobic groups) and if the barrier 3 is cation selective then electrode 1 should be cathodic and electrode 2 anodic. It will be obvious that if the barrier 3 is instead anion selective, the potential of the electrodes must be reversed.

If dissociation of the ligate(s) is effected by an electrically controlled change in ionic strength as described above and if the barrier 3 is ion-selective then it may be advantageous if the barrier 4 has the opposite ion-selectivity, i.e. if barrier 3 is cation-selective then barrier 4 may be advantageously anion-selective.

Depending upon the composition of the liquids in compartments 6, 7 and 8, the heat generated by the applied current may be excessive in which case the contents of compartments 7 and 8 may be advantageously recirculated through an external heat exchanger, absorbing heat from compartment 6 through barriers 3 and 4.

Referring again to FIG. 2, the transfer of the dissociating agent may be continued through only one barrier until the pH, ionic strength or concentration of chaotropic agent is sufficient throughout the body of biospecific fibrous substrate to result in dissociation of the ligate(s) from the ligand(s). After an appropriate interval the contents of compartment 6 are flushed out.

Alternatively the dissociating agent may first be transferred from compartment 7 at least halfway through the body of biospecific substrate in compartment 6 and after an appropriate interval (with or without passage of a maintenance current) the contents of compartment 6 are swept out. The polarity of the electric current may subsequently be reversed and the dissociating agent (generally the same one used in the prior step) transferred electrically from compartment 8 again at least halfway through the body of biospecific substrate 5 and after an appropriate interval the contents of compartment 6 again swept out. Such step-wise procedure can provide a particularly gentle dissociating environment.

In another embodiment, one of barriers 3 and 4 is ion selective and the other has alternatively no ion selectivity, substantially less selectivity of the same sign or has selectivity of the opposite sign. In such case the direction of the applied electric current is such as to increase the ionic strength in compartment 6 if the ligate will be dissociated by such an increase. On the other hand if the ligate will be dissociated by a decrease in ionic strength, then the direction of the electric current should be such as to decrease the ionic strength in compartment 6.

Figure 3:
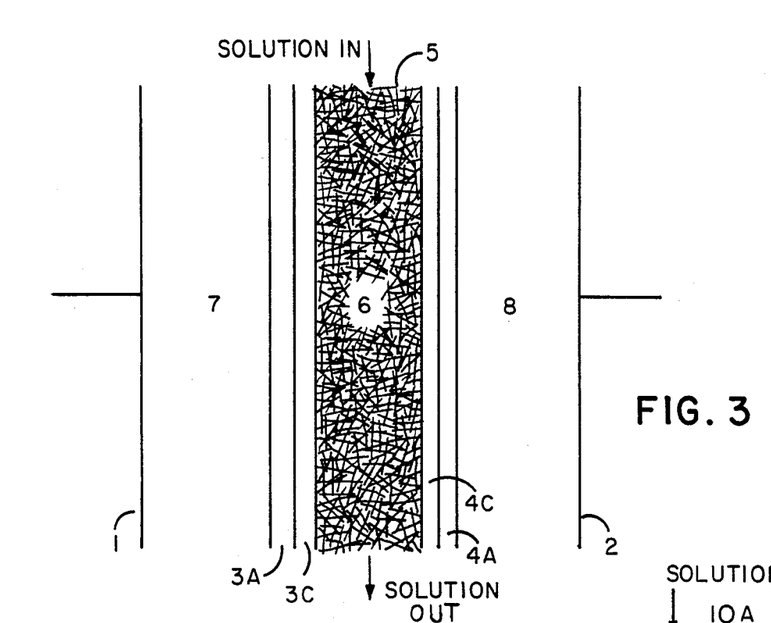
FIG. 3 is a schematic representation of a third embodiment of an apparatus in accordance with the present invention, having water-splitting electrolytically conducting barriers and a biospecific sorbing fibrous substrate.

Yet another embodiment of the invention may be described with respect to FIG. 3 in which either or both of the barriers 3 and 4 are bipolar ion selective membranes (for example as described in U.S. Pat. No. 3,562,139-Leitz). For example regions $3a$ and $4a$ may comprise anion selective material and regions $3c$ and $4c$ cation selective material. When electrode 1 is made anodic and electrode 2 cathodic, the interface between regions $3a$ and $3c$, rapidly becomes substantially depleted of electrolyte. If passage of electric current is thereafter continued it will be carried through regions $3a$ by hydroxide ions resulting from the dissociation of water at or near the interface between regions $3a$ and $3c$. Current through region $3c$ will be carried by hydrogen ions (resulting from such water dissociation) at least halfway through the body of biospecific fibrous substrate in compartment 6 resulting in dissociation of ligate-ligand complexes. After an appropriate interval, the contents of compartment 5 will be swept out together with the dissociated ligate. The direction of the electric current may then be reversed if desired, causing hydrogen ions generated at the interface between regions $4a$ and $4c$ to dissociate ligand-ligate complexes at least in the biospecific substrate in the region adjacent to barrier 4. After an appropriate interval the contents of compartment 6 are again swept out.

It can be appreciated that if a single pass of the liquid through one apparatus as described above does not adsorb the required amount of the component of interest, a series of apparatuses can be arranged in which the liquid flows in series through each, with each adsorbing a portion of the said component. Each apparatus may instead contain two or more hydraulic stages between electrodes as is well known in the electrodialysis art. Alternatively, a single stage unit can be employed by which the liquid is continuously recirculated therein in a batch mode until the required adsorption is attained. The number of compartments in each electrical stage and the number of stages in series can of course be varied depending upon the particular application and production rate required.

If more than one absorption stage is used in series or parallel, then it may be appropriate to stage also the desorption step, preferably countercurrently and in series. For example, the ligate in the last absorption stage may be dissociated first and the liquid contents of compartment(s) 6 in such stage sent to compartment(s) 6 in the next prior absorption stage after which the ligate in such step is dissociated. The procedure is repeated stage by stage countercurrently, thereby building up the concentration of recovered ligate in a small volume of liquid.

Although the process and apparatus of this invention have been described for the sake of simplicity in terms of barriers and electrodes which are planar, flat sheets, it will be understood that other configurations may be advantageously used. For example, referring again to FIG. 2, the electrodes and barriers may be arranged as concentric cylinders, in which case the central electrode may have the form of a rod or wire.

A further embodiment of the invention may be described with reference to the apparatus of FIG. 4 in which 6 represents a cavity containing a body of hollow fibers 5 terminated on at least the entrance end of the fibers by a tube sheet 9. At least the entrance tube sheet is fitted or sealed into the apparatus sufficiently so that all or a substantial fraction of solution entering the apparatus through conduit 10a passes though the interior of the hollow fibers. Although the hollow fibers are shown as a tight bundle of straight, parallel fibers oriented along the long axis of the cavity 6, other configurations are contemplated within the scope of the invention. For example, the axis of the fibers may be at an angle or even perpendicular to the long axes of the container; or the bundle of fibers may be arranged in a helix from one end of the cavity to the other; or the bundle may be bent back upon itself one or more times. It will be obvious that if bent back an odd number of times the entrance and exit channels will be at the same end of the apparatus, means for accomplishing such being well within the skill of a mechanic.

The biospecifically sorbing surface may be limited to the interior of the hollow fiber, to the outside or may include both surfaces. If the external surfaces are biospecifically sorbing then communication with them may be achieved through channels 11a and 11b. If both interior and exterior surfaces are used, then in principle the biospecific area per unit volume will be approximately twice that if only one of the surfaces is active.

Figure 4:
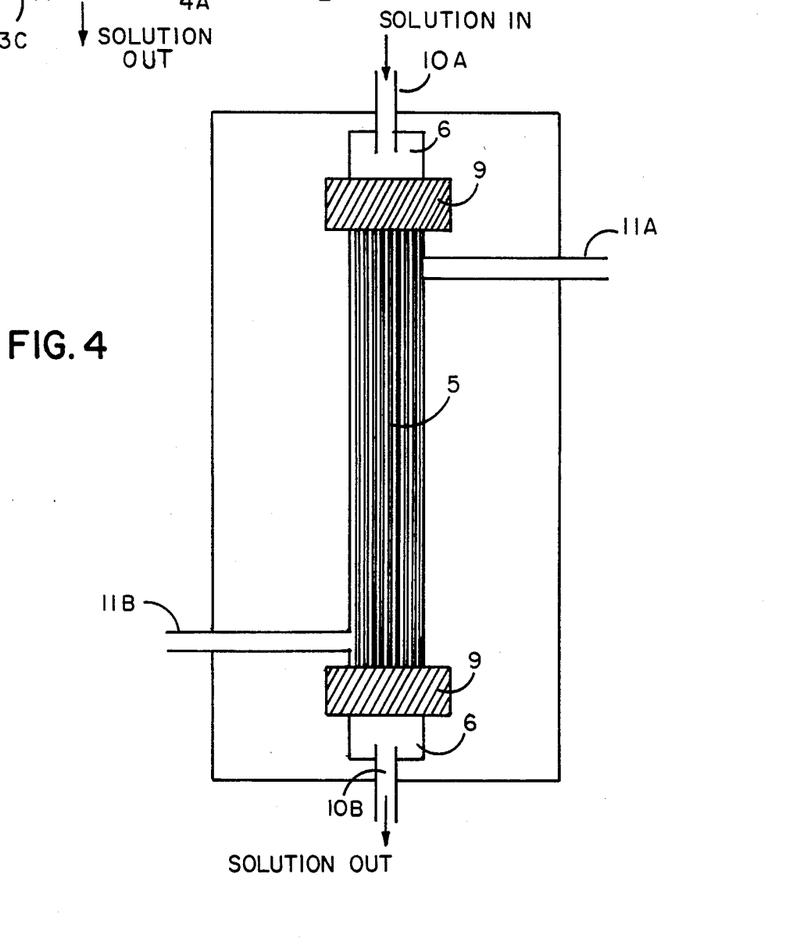
FIG. 4 is a schematic representation of a fourth embodiment of an apparatus in accordance with the present invention, having a biospecific sorbing, hollow, fibrous substrate.

Several modes of operation are contemplated:

(a) The fibers are substantially impermeable to ions, small molecules and large molecules and the interior of the fibers is biospecifically sorbing, in which case both sorption and desorption must be accomplished by appropriate liquids introduced into the interior of the fibers;

(b) The fibers are substantially impermeable to ions, small molecules and large molecules and the exterior of the fibers is biospecifically sorbing, in which case both sorption and desorption must be accomplished by appropriate liquids introduced to the exterior of the fibers or if the faces of the apparatus of FIG. 4 are exposed it can be inserted in place of the central compartment 6 in the apparatus of FIGS. 2 or 3. In such case desorption may be carried out substantially as described in connection with the discussion of the apparatus of FIGS. 2 and 3;

(c) The fibers are substantially permeable to ions and small molecules, but substantially impermeable to large molecules, in which case sorption must be accomplished by appropriate liquids introduced to whichever side (or both) of the fibers that are biospecifically sorbing. If desorption is facilitated by ions and/or small molecules then the fibers can be contacted with the appropriate liquid on either or both sides or, alternatively, the apparatus can be inserted in place of the central compartment 6 in the apparatuses of FIGS. 2 and 3 as described above.

(d) The fibers are substantially permeable to ions and small and large molecules in which case the sorption is preferably accomplished by appropriate liquids introduced to whichever side (or both) of the fibers that are biospecifically sorbing but may be introduced to either or both sides with little penalty. The fibers can also generally be contacted with the appropriate desorption facilitating solution on either or both sides or alternatively, the apparatus can be inserted in place of the central compartment 6 in the apparatuses of FIGS. 2 and 3 as described above.

It will be understood that the choice of fiber diameter, wall thickness, and length will depend upon many factors including: the pressure available, the tensile strength of the material of the fiber, the rate of diffusion of the target ligate and the rate of ligand-ligate binding at the fiber walls. It will be obvious, however, that if the internal diameter of a fiber is less than about 0.1 mm, the characteristic diffusion time of a target ligate to and/or from the ligands even at low flows will be less than that to and/or from a biospecific membrane under even well stirred conditions and less than that to and/or from the interior surfaces of biospecific granules or beads having diameters greater than 0.1 mm.

It will also be understood that some desirable fibers may have some permeability to liquid in which case any permeate may be drained or rinsed from the apparatus through conduits 10a, 10b, 11a, and/or 11b as appropriate. The following non-limiting examples illustrate the present invention:

EXAMPLE 1

Cotton gauze is reacted at an alkaline pH with cyanogen bromide and then with L-lysine in the manner well-known in the art to introduce a high density of L-lysine ligands coupled to the gauze. The gauze is packed into a small glass column. The column is rinsed with about 0.1 molar sodium hydrogen phosphate buffer having a pH of about 7.4. Human blood plasma is diluted 1:1 with distilled water and recirculated through the column several times. The column is drained and then rinsed for several minutes with about 0.3 molar sodium hydrogen phosphate buffer having a pH of about 7.4 and again drained. A solution containing about 0.3 molar sodium hydrogen phosphate and 0.3 molar epsilon-aminocaproic acid (adjusted to pH about 7.4) is recirculated through the column several times and is found to contain a substantial fraction of the plasminogen removed from the plasma.

EXAMPLE 2

A 3 compartment apparatus is constructed in accordance with FIG. 1. Barrier 3 is a CR61 AZL cation selective membrane and barrier 4 an AR204 SXZL anion selective membrane, both membranes available from Ionics, Incorporated, Watertown, Mass. U.S.A. The barriers are arranged vertically and have dimensions of about 15.2 by 7.6 cm and are about 0.06 cm thick reinforced with a fabric woven from spun, modacrylic staple. The electrodes are platinized titanium of the same dimensions. The electrodes are separated from the barriers by open spacers fabricated from low density polyethylene and having a thickness of about 0.1 cm and an effective area of about 15 cm. The barriers are separated from each other by a composite of five similar spaces, i.e. the distance between the barriers is about 0.5 cm. Channels connect with the central chamber at both top and bottom.

The central chamber is loosely filled with cotton gauze having a high density of L-lysine groups coupled to the gauze by cyanogen bromide. The central compartment is rinsed with about 0.1 molar sodium hydrogen phosphate buffer having a pH of about 7.4. Twenty ml. of human blood plasma is diluted 1:1 with distilled water and recirculated through the central compartment. The solution is drained and the central compartment rinsed with 0.3 M sodium hydrogen phosphate buffer having a pH of about 7.4. The buffer is drained from the compartment. A 0.3 molar solution of epsilon-aminocaproic acid adjusted to a pH of about 11 with sodium hydroxide is circulated through the cathode compartment and 0.3 molar epsilon amino-caproic acid solution adjusted to a pH of about 4.5 with hydrochloric acid is circulated through the anode compartment. A current of about 0.5 ampere is passed for several minutes. The contents of the center compartment 6 are flushed out and found to contain a substantial fraction of the plasminogen removed from the plasma. The gauze is removed from the central compartment and recovered.

EXAMPLE 3

The gauze recovered from Example 2 is packed in a glass column, rinsed with 0.3 molar epsilon-aminocaproic acid and then with 0.3 molar sodium hydrogen phosphate. Human blood plasma diluted 1:1 with distilled water is recirculated through the column. The column is drained and rinsed with sodium hydrogen phosphate buffer having a pH of about 7.4. The gauze is then transferred to the central compartment of the apparatus of Example 2 and the plasminogen desorbed substantially as described therein. A substantial fraction of the plasminogen removed from the plasma is recovered.

EXAMPLE 4

A filter cartridge wound with cotton yarn is activated with cyanogen bromide and L-lysine. The cartridge is rinsed with 0.3 molar sodium hydrogen phosphate having a pH of about 7.4. Human blood plasma diluted 1:1 with distilled water is recirculated through the cartridge. The cartridge is drained and then rinsed with 0.3 molar sodium hydrogen phosphate having a pH of about 7.4 and again drained. A 0.3 molar solution of epsilon-aminocaproic acid is then recirculated through the cartridge several times. The epsilonaminocaproic acid is found to contain a substantial fraction of the plasminogen removed from the plama.

EXAMPLE 5

A filter cartridge wound with cotton yarn is activated with cyanogen bromide and L-lysine and then contacted with diluted human plasma, all as described in Example 4. The cartridge is drained and then rinsed with 0.3 molar sodium hydrogen phosphate solution having a pH of about 7.4. The cartridge is removed from its holder and wrapped with an anion selective membrane. A cylindrical cation exchange membrane is fitted into the central cavity of the cartridge and held in place by a rubber stopper inserted at the lower end of the cavity. The cartridge is placed in a glass cylinder closed at the lower end. Stainless steel screen is inserted as a cathode around the inside of the glass cylinder and a platinized titanium rod anode placed in the central cavity of the cartridge. The cathode space is filled with about 0.3 M epsilon-aminocaproic acid adjusted to a pH of about 4.5 with hydrochloric acid and the anode space with about 0.3 M episilon-aminocaproic acid adjusted to about pH 11 with sodium hydroxide. A direct current of about 20 amperes is passed for several minutes. The cartridge is immediately returned to its holder and flushed with substantially two displacement volumes of 0.3 molar epsilon-aminocaproic acid. It is found that the aminocaproic acid solution contains a substantial fraction of the plasminogen removed from the plasma in a more concentrated form than that found in Example 4.

EXAMPLE 6

A rectangular bundle of cellulose hemodialysis hollow fibers about 1.5 cm wide and 0.5 cm deep are encapsulated at each end with epoxy resin. The resin caps are carefully trimmed at their far ends to make tube sheets about 0.5 cm deep, 2.5 cm wide and about 1 cm long in the direction of the fibers as illustrated in FIG. 4. The distance between inside edges of the tube sheets is about 9.2 cm. The resulting bundle is inserted into a plastic frame machined from a block of fiberglass reinforced epoxy about 0.5 cm thick, 7.6 cm wide and 15.2 cm long. The tube sheets are glued into the epoxy frame as are entrance and exit tubings as shown in the figure. Thin gum rubber sheets having a central opening only over the exposed fibers are glued over each face of the frame and tube sheets. Polymethyl methacrylate sheet is placed over each face of the frame and held in place by the rods and thumb nuts, making a central fiber containing chamber sealed by the gum rubber. The interior of the fibers is activated with tosyl chloride. Both the interior and exterior of the fibers are rinsed with a phosphate chloride buffer and then a solution of anti-factor VIIIc in phosphate/chloride buffer is recirculated through the interior of the fibers for about 24 hours at about 4° C. The fibers are drained and both inside and outside rinsed with buffer solution. Cryoprecipitate from human blood plasma is dissolved in phosphate/chloride buffer to give a solution having about 20 mg of protein per ml. The solution is recirculated through the interior of the fibers. The partially depleted cryoprecipitate solution is drained from the fibers which are then rinsed both inside and outside with fresh buffer. An approximately 3 molar solution of sodium thiocyanate of about pH 7 is recirculated through the interior of the fibers for several minutes and immediately dialyzed to reduce the concentration of chaotropic agent as rapidly as possible. The recovered desorbate is found to contain a substantial fraction of the Factor VIIIc removed from the cryoprecipitate.

EXAMPLE 7

The experiment of Example 6 is repeated except that the chaotropic solution is recirculated through the outside of the fibers. After several minutes the solution in the inside of the fibers is rapidly flushed with about 3 volumes of phosphate/chloride buffer (that is about 3 times the estimated total interior volume of the fibers). The recovered buffer is found to contain a substantial fraction of the Factor VIIIc removed from the cryoprecipitate.

EXAMPLE 8

The experiment of Example 6 is repeated except that after the cryoprecipitate solution is drained from the fibers and they are rinsed both inside and outside with fresh buffer, the polymethyl methacrylate plates are removed and the frame is substituted for the central compartment of the apparatus of Example 2. The inside and outside of the fibers are filled with phosphate/chloride buffer. An approximately 3 molar solution of sodium thiocyanate of about pH 7 is recirculated through compartments 7 and 8. Electrode 1 is made anodic and electrode 2 cathodic. A current of about 1 ampere is passed for several minutes. Thereafter the contents of the interior of the fibers are rapidly flushed out with about 3 volumes of phosphate/chloride buffer and immediately dialyzed to reduce the concentration of chaotropic agent as rapidly as possible. The recovered desorbate is found to contain a substantial fraction of the Factor VIIIc removed from the cryoprecipitate.

While the invention has been herein shown and described in what is presently conceived to be the most practical and preferred embodiments thereof, it will be apparent to those of ordinary skill in the art that many modifications may be made thereof within the scope of the invention, which scope is to be accorded the broadest interpretation of the appended claims so as to encompass all equivalent assemblies and methods.

What is claimed is:

1. A method for recovering biospecifically, sorbable components previously sorbed on a body of filaments having biospecific sorbing properties for said components comprising:
    (a) passing a direct electric current through said body of filaments in a direction substantially parallel to the smallest dimension of said body thereby facilitating the desorption of at least one of said biospecifically, sorbable components from said filaments;
    (b) removing said desorbed components from contact with said filaments.

2. A method for recovering components sorbed on a body of filaments highly selective for the sorption of said components comprising,
    (a) passing a direct electric current through said body of filaments and through an ion-permeable barrier which is positioned juxtaposed with said body of filaments, said current passed in a direction substantially parallel to the smallest dimension of said juxtaposed barrier, thereby facilitating the desorption of at least one of said selected components from said filaments;
    (b) removing said desorbed components from contact with said filaments.

3. A method according to claim 2 in which said filaments contain ligands selected from the group consisting of enzyme inhibitors, enzyme substrate analogues, coenzymes, apoenzyme polymeric substrates, enzymes, nucleic acid complementary strands, haptens, antibodies, monosaccharides, polysaccharides, lectins, small target compounds for binding proteins, binding proteins, amino-benzamidine, 5'-adenosine monophosphate, S. aureus Protein A, hormones, hormone receptors and immobilized textile dyes.

4. A method of recovering components dispersed in an aqueous solution comprising:
    (a) contacting said solution as a first solution with body of fibers highly selective for the sorption of at least one of said selected components whereby a substantial fraction of said selected component or components is sorbed by said fibers;
    (b) removing said first solution from contact with said fibers,
    (c) contacting said fibers with a second aqueous solution,
    (d) passing a direct electric current through said body of fibers, said second solution and an ion-permeable substantially hydraulically impermeable barrier in contact with said body of fibers in a direction substantially parallel to the smallest dimension of said barrier thereby facilitating the desorption of at least one of said selected components from the said fibers to said second solution and
    (e) removing said second solution from contact with said fibers.

5. Apparatus for recovering biospecifically, sorbable components previously sorbed on a body of hair-like objects having biospecific sorbing properties for said components comprising:
    (a) means for passing a direct electric current through said body of hair-like objects in a direction substantially parallel to the smallest dimension of said body, thereby to facilitate the desorption of at least one of said biospecifically, sorbable components from said body, and
    (b) means for removing said desorbed components from contact with said hair-like objects.

6. Apparatus according to claim 5 in which said hair-like objects are hollow.

7. Apparatus according to claim 5 in which said hair-like objects are porous.

8. Apparatus for recovering components sorbed on a body of thread-like structures highly selective for the sorption of said components comprising:
    (a) an electrolytically conducting, substantially hydraulically impermeable barrier juxtaposed to said body of thread-like structures,
    (b) means for contacting said body with an aqueous receiving solution,
    (c) means for passing a direct electric current through said barrier and said body in a direction substantially parallel to the smallest dimension of said barrier thereby to facilitate the desorption of at least one of said selected components from said body, and
    (d) means for removing said aqueous receiving solution from contact with said body.

9. Apparatus according to claim 8 in which said barrier has the form of a cylinder.

10. Apparatus according to claim 8 in which said barrier has the form of a spiral.

11. Apparatus according to claim 8 in which said barrier is selected from the group consisting of non-selective membranes, sheets of hydrous gels and porous sheets having average pore sizes of less than about 10 micrometers.

12. Apparatus according to claim 8 in which said barrier is a macro-reticular ion-selective membrane.

13. Apparatus according to claim 8 in which said barrier is an ion-selective membrane.

14. Apparatus according to claim 8 in which said barrier is a bipolar ion-selective membrane.

15. Apparatus according to claim 8 in which said barrier is an ion-selective membrane having ligands attached to a macroreticular surface.

16. Apparatus for recovering components dispersed in a first aqueous solution comprising:
    (a) a body of fibers highly selective for the sorption of at least one of said components,
    (b) means for contacting said body with said first solution and for removing said first solution from contact with said body,
    (c) means for contacting said body with second aqueous solution as a receiving solution, said receiving solution comprising means for facilitating the desorption of at least one of said selected components from the body into said second solution, and
    (d) means for removing said second solution from contact with said body.

17. Apparatus according to claim 16 in which said body is in the form of a filter cartridge.

18. Apparatus according to claim 16 in which said body has the form of a filter cartridge wrapped with fibers selected from the group consisting of string, yarn, tow, filtermasse, batting, roving, sliver, cake-of-fibers, woven fabric, knitted fabric, non-woven fabric, fiber-mat, felt, needled felt, screen, gauze and mixtures thereof.

19. Apparatus according to claim 16 in which the body of fibers is embedded at least at one end in a tube sheet.

20. Apparatus for recovering components dispersed in a first aqueous solution comprising:
(a) a body of hollow fibers highly selective in at least the interior of said fibers for the sorption of at least one of said components, said body of fibers being embedded in at least one end in a tube sheet,
(b) means for contacting the interior of said fibers with a second aqueous solution as a receiving solution which solution comprises agents for facilitating the desorption of at least one of said selected components from said body into said second solution, and
(d) means for removing said second solution from contact with said body.

21. Apparatus according to claim 20 in which the hollow fibers are substantially impermeable to said selected components.

22. Apparatus according to claim 20 in which the hollow fibers are permeable to the said agent for facilitating the desorption of at least one of said selected components from said body of hollow fibers into said second solution.

23. Apparatus for recovering components dispersed in a first aqueous solution comprising:
(a) a body of hollow fibers highly selective on at least at the interior surfaces of said fibers for the sorption of at least one of said components, said body of fibers being embedded at least one end in a tube sheet,
(b) means for contacting at least the interior of said fibers with said first solution and means for removing said first solution from contact with said body,
(c) means for passing a direct electric current through said body in a direction substantially non-parellel to the major axes of such fibers, thereby to facilitate the desorption of at least one of said selected components from said body, and
(d) means for removing said desorbed components from contact with said body.

* * * * *